(12) United States Patent
Mehrabi et al.

(10) Patent No.: US 12,251,237 B2
(45) Date of Patent: Mar. 18, 2025

(54) SYSTEM FOR PROCESSING SIGNALS FROM A BALLOON CATHETER THAT USES SNAP-IN CONNECTION

(71) Applicant: BIOTRONIK AG, Bülach (CH)

(72) Inventors: Azadeh Mehrabi, Meilen (CH); Carina Haber, Singen (DE)

(73) Assignee: BIOTRONIK AG, Buelach (CH)

( * ) Notice: Subject to any disclaimer, the term of this patent is extended or adjusted under 35 U.S.C. 154(b) by 509 days.

(21) Appl. No.: 17/634,318

(22) PCT Filed: Jul. 20, 2020

(86) PCT No.: PCT/EP2020/070402
§ 371 (c)(1),
(2) Date: Feb. 10, 2022

(87) PCT Pub. No.: WO2021/028151
PCT Pub. Date: Feb. 18, 2021

(65) Prior Publication Data
US 2022/0280115 A1 Sep. 8, 2022

(30) Foreign Application Priority Data
Aug. 14, 2019 (EP) ..................... 19191679

(51) Int. Cl.
*A61B 5/00* (2006.01)
(52) U.S. Cl.
CPC .... *A61B 5/6853* (2013.01); *A61B 2560/0223* (2013.01); *A61B 2560/029* (2013.01); *A61B 2560/0443* (2013.01); *A61M 2205/502* (2013.01)

(58) Field of Classification Search
None
See application file for complete search history.

(56) References Cited

U.S. PATENT DOCUMENTS

| | | | |
|---|---|---|---|
| 2007/0083111 A1 | 4/2007 | Hossack et al. | |
| 2009/0315684 A1* | 12/2009 | Sacco | A61M 25/0017 340/10.6 |
| 2010/0063512 A1* | 3/2010 | Braga | A61B 17/32 606/108 |
| 2013/0211221 A1 | 8/2013 | Sunnarborg et al. | |

(Continued)

FOREIGN PATENT DOCUMENTS

| | | |
|---|---|---|
| WO | 03020110 A2 | 3/2003 |
| WO | 2012088564 A1 | 7/2012 |
| WO | 2016181316 A1 | 11/2016 |

OTHER PUBLICATIONS

EP Office Action for corresponding EP Application No. 20740332.0-1113, dated Mar. 19, 2024.

(Continued)

*Primary Examiner* — Bernard G Lindsay
(74) *Attorney, Agent, or Firm* — Greer, Burns & Crain, Ltd.; Steven P. Fallon (57) ABSTRACT

A processing system including a processing unit is configured to be connected to a catheter in a releasable fashion via a connecter portion of a housing. The processing unit is configured to exchange data with a component of the catheter and at least one of a database, a computer network, and a computer device. The processing unit includes an integrated circuit for processing the data.

17 Claims, 5 Drawing Sheets

(56) References Cited

U.S. PATENT DOCUMENTS

| | | |
|---|---|---|
| 2014/0187985 A1 | 7/2014 | Corl et al. |
| 2016/0136356 A1* | 5/2016 | Ribble ............... A61B 5/14552 |
| | | 705/2 |
| 2017/0165454 A1* | 6/2017 | Tuohy ................. A61M 31/005 |
| 2018/0236204 A1* | 8/2018 | Milhous ............. A61B 18/1492 |

OTHER PUBLICATIONS

International Search Report and Written Opinion from the corresponding International Patent Application No. PCT/EP2020/070402, dated Sep. 30, 2020.

* cited by examiner

SYSTEM FOR PROCESSING SIGNALS FROM A BALLOON CATHETER THAT USES SNAP-IN CONNECTION

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2020/070402, which was filed Jul. 20, 2020, which application claimed priority from European Application Serial Number 19191679.0, which was filed Aug. 14, 2019.

FIELD OF THE INVENTION

A field of the invention is balloon catheter systems for implanting a stent into a vessel, in particular for dilating a stenosis of the vessel, and particularly to a processing unit, a system and a method for automatically recognizing a catheter and processing measurement data of a sensor of the catheter.

BACKGROUND

Sensors, which are arranged e.g. on a balloon of a catheter, can have different sensor signals with the same balloon parameters due to minimal deviations of the balloon shapes and arrangement of the sensor on the respective balloon.

WO 2009/051781 describes an in vivo calibration of blood pressure sensors assigned to a balloon using electronically stored correction data. WO2015/010064 discloses a blood pressure measurement based on an infrared sensor mounted on a balloon catheter and a calibration with corresponding data exchange via an analog/digital converter.

SUMMARY OF THE INVENTION

The present invention provides a processing system including a processing unit. A housing of the system is releasably connectable to a catheter via a connector of the housing. The processing unit is configured to identify different catheters or balloons. The system provides a reliable processing, for instance calibration, of the measurement data of the sensor is ensured in a user-friendly way.

A preferred processing system includes a processing unit and is configured to be connected to a catheter in a releasable fashion via a connecter portion of a housing. The processing unit is configured to exchange data with a component of the catheter and at least one of a database, a computer network, and a computer device. The processing unit includes an integrated circuit for processing the data.

BRIEF DESCRIPTION OF THE DRAWINGS

In the following, the embodiments as well as further features and advantages of the present invention will be explained with reference to the Figures, wherein.

DETAILED DESCRIPTION OF THE PREFERRED EMBODIMENTS

A housing of a system of the invention contains a processing unit and is provided with a connector portion insertable into an opening of a proximal end portion of the catheter. Proximal means that said end portion is closer to a person operating the catheter than an opposite distal end portion of the outer shaft insertable into the patient.

Further the connector portion is provided with electrically conductive contacts each configured to be electrically connected to an associated contact of the catheter when the connector portion is inserted into said opening of the proximal end portion of the catheter.

Further the connector portion surrounds a through opening of the processing unit, the through opening being adapted to open into a lumen of the catheter, e.g. when the connector portion is inserted into said opening of the proximal end portion of the catheter.

According to the invention, the processing unit includes a through opening being adapted to open into a lumen of the catheter. Thereby the processing unit can be easily coupled to the catheter. Usually the proximal end portion of a catheter includes a hub or Luer connector providing access to at least one lumen of the catheter. The inventive processing unit can be attached to the proximal end of the catheter in a way, that the through opening of the processing unit opens into said lumen of the catheter and thereby the lumen could be accessed via the processing unit. Thereby the catheter can be easily equipped with the processing unit without changing the performance or the handling of the catheter.

Further, according to a design of the processing unit, the connector portion forms a Luer connector. In this embodiment of the invention the processing unit itself provides a standard Luer connections. In particular, if the catheter already includes a Luer connector, the processing unit can be attached to the Luer connector of the catheter and thereby providing a Luer connection as well.

In a preferred embodiment the connector portion is insertable into an opening of a proximal end portion of the outer shaft of the catheter.

Furthermore the connector portion surrounds a through opening of the processing unit, the through opening may be adapted to open into an inflation lumen or a guidewire lumen of the catheter, e.g. when the connector portion is inserted into said opening of the proximal end portion of the catheter.

Particularly, according to an embodiment, the processing unit is configured to be mechanically connected to the catheter in a releasable fashion. The mechanical connection of the processing unit to the catheter in a releasable fashion allows the combination of one processing unit with multiple catheters of different types. The processing unit is therefore configured as a reusable processing unit.

According to an embodiment of the invention, the processing unit is configured to be mechanically connected to a balloon catheter, a catheter suitable for implanting an intraluminal prosthesis, in particular a stent, a catheter suitable for implanting a valve prosthesis, in particular a heart valve prosthesis or a venous valve prosthesis, or a catheter suitable for implanting a closure device.

Furthermore, according to an embodiment, said component is one or more of: a sensor of the catheter, an inflation pump of the catheter for inflating a balloon of the catheter.

Particularly, in an embodiment, the sensor can be a sensor configured to measure a parameter of the balloon, in particular one of the following: a circumference, a radius, a volume. The parameter may also be a parameter derived from one of the said afore-mentioned parameters. In particular, the sensor may be a strain gauge. Furthermore, the sensor may be designed to measure an impedance in an embodiment. Furthermore, the sensor can be a force sensor that measures a force acting on the balloon. Other sensors are also conceivable. The processing unit could be configured to exchange data with one or more components (sensors) of the same or of a different kind.

Further, according to an embodiment of the processing unit, the latter is configured to recognize the catheter (among a plurality of different catheters to which the processing unit is releasably connectable) using an identifier code of the catheter when the catheter is connected to the processing unit.

Furthermore, according to an embodiment, the processing unit includes a memory for storing information relating to different catheters to which the processing unit is connectable.

Further, in an embodiment, the processing unit is configured to match the identifier code with information stored in said memory of the processing unit. Alternatively or in addition, the processing unit is configured to match the identifier code with information stored in a remote database implemented on a computer network (i.e. cloud) to recognize the catheter among a plurality of different catheters to which the processing unit is releasably connectable.

Further, according to an embodiment, the processing unit is configured to retrieve information on the recognized catheter from the memory of the processing unit and/or from the remote database and to transmit said retrieved information to a computer device to display said information on a display of the computer device to the user (e.g. physician) that operates the catheter.

Furthermore, according to an embodiment, the processing unit is configured to retrieve calibration data corresponding to the recognized catheter from a memory of the processing unit or from the remote database, and to calibrate the measurement data of the sensor using the calibration data.

According to a further aspect, a system is disclosed, the system including a processing unit according to the present invention and a catheter including a sensor for measuring a parameter relating to the catheter. The system of the invention includes two major parts, a processing unit and a catheter. Since the processing unit is connected to the catheter in a releasable fashion, the processing unit is reusable with various catheters. The catheter and the processing unit of the invention are configured for a releasable mechanical connection between each other.

In particular the catheter is a balloon catheter, a catheter suitable for implanting an intraluminal prosthesis, in particular a stent, a catheter suitable for implanting a valve prosthesis, in particular a heart valve prosthesis or a venous valve prosthesis, or a catheter suitable for implanting a closure device.

Particularly, the sensor can be one of the sensors stated above. According to a further embodiment, the catheter can include an inflation pump configured to inflate a balloon of the catheter. Furthermore, the catheter can include a plurality of sensors, particularly different sensors. The respective sensor can e.g. be one of the above stated sensors.

According to an embodiment of the system, the system further includes said computer device, wherein the computer device is configured to communicate with the processing unit (particularly in a wireless fashion). The communication is not necessarily bi-directional but a bi-directional communication is preferred.

Particularly, the computer device is a mobile hand-held device such as a smartphone, but can also be any other suitable computer such as a laptop, a tablet or a desktop computer.

The computer device includes a user interface and a display [configured for graphically displaying information]. Particularly, for conducting user input into user interface and for displaying information on the display, the computer device can be configured to execute a corresponding computer program.

Further, according to an embodiment, the computer device is configured to scan the identifier code from the catheter or a package of the catheter, to which catheter the processing unit is to be connected or to which the processing unit is connected (or connectable). Alternatively, or in addition, the user interface is configured for receiving the identifier code as an (e.g. manual) user input.

According to a further embodiment of the system, the latter further includes a database executed on a computer network (the system may also include the computer network and the database thereon).

Particularly, the processing unit is configured to compare match the identifier code with information stored in said database to recognize the catheter among a plurality of different catheters to which the processing unit is releasably connectable.

Further, according to an embodiment of the system, the processing unit is configured to transmit the retrieved information relating to the catheter to the computer device, which is configured to display said information via said display.

According to an embodiment, said retrieved information includes at least one of: a designation of the catheter, instruction for use of the catheter, a type of the catheter, a list of measurements that the catheter is configured to carry out (e.g. using the sensor).

Furthermore, according to an embodiment, the user interface is configured to receive an input by the user to confirm use of the recognized catheter, and particularly to start a procedure guided by the system during which the recognized catheter is used.

According to a further embodiment of the system, the processing unit is configured to transmit measurement data received from the sensor of the recognized catheter to the computer device to display the measurement data on said display during operation of the catheter.

Furthermore, in an embodiment of the system, the processing unit is configured to store the measurement data received from the sensor and/or data relating to a procedure performed with the catheter in the memory of the processing unit and/or in said database.

Yet another aspect of the present invention relates to a method using a system according to the present invention, wherein the method includes the steps of:

connecting the processing unit to the catheter,
automatically recognizing the catheter using an identifier code of the catheter, retrieving information with the processing unit on the recognized catheter from the memory of the processing unit or from the database, and displaying measurement data transmitted by the sensor of the catheter to the processing unit on the display of the computer device.

Particularly, the measurement data is continuously displayed on the display during operation of the catheter so that the system can be efficiently used to guide the procedure or use of the catheter.

According to an embodiment of the method, the step of automatically recognizing the catheter includes the further step of comparing, particularly matching, the identifier code with information stored in the memory of the processing unit and/or in the database.

According to an embodiment, the method includes the further step of scanning the identifier code from the catheter or from a package of the catheter (e.g. by means of the computer device or a scanner connected thereto) or inputting the identifier code into the user interface of the computer device.

According to an embodiment, the method includes the further step of displaying the retrieved information about the recognized catheter on the display of the computer device, particularly before the step of displaying said measurement data.

According to an embodiment, the method includes the further step of confirming the displayed information using the user interface of the computer device (e.g. so as to start a procedure using the recognized catheter), particularly before the step of displaying said measurement data.

According to a further embodiment, said measurement data of the sensor and or data relating to a procedure performed using the catheter is also stored in the memory of the processing device and/or in the database.

According to a further embodiment, the method includes the further step of analyzing data transmitted to the database.

Figure 1:
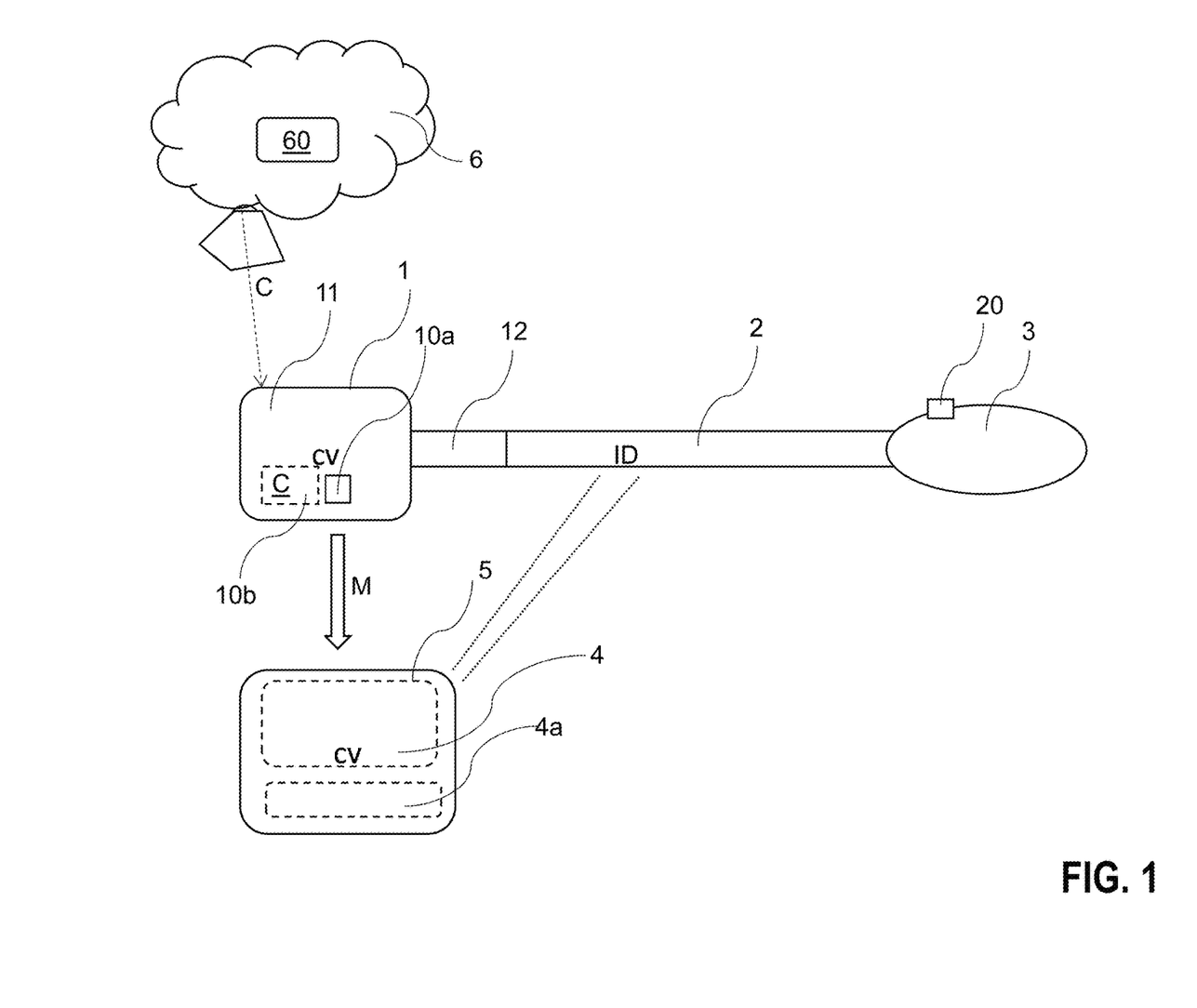
FIG. 1 shows a schematic illustration of an embodiment of a processing device/system according to the present invention.

FIG. 1 shows an embodiment of a processing system with a processing unit 1 according to the present invention. The processing unit 1 is configured to be connected to a catheter 2 in a releasable fashion and configured to communicate and in particular exchange data with at least one of: a component of the catheter 20, a database 60, a computer network 6 (cf. also FIGS. 2 and 3), a computer device 5, wherein the processing unit 1 includes an integrated circuit 10a for processing said data. The communication is not necessarily bi-directional but preferred in this embodiment. The integrated circuit 10a can be a microprocessor or can include such a processor or a comparable means.

Furthermore, the processing unit 1 can include a housing 11 for accommodating components of the processing unit 1 such as the integrated circuit 10a, wherein the housing 11 may include a connector 12 for connecting the housing 11 of the processing unit 1 in a releasable fashion (e.g. mechanically) to the catheter 2 (e.g. at a proximal end of the catheter 2). The catheter 2 can be a balloon catheter that includes a balloon 3 (e.g. for performing an angioplasty or implanting an expandable implant into a body lumen). However, the invention applies to all kinds of catheters 2. According to FIG. 1, said component 20 can be a sensor 20 that measures a parameter relating to the catheter 2, such as a diameter of the balloon 3 or another quantity of interest.

Particularly, for using the processing unit 1, the latter is mechanically connected to the catheter 2 using e.g. said connector 12, which preferably also establishes the necessary electrical connections between the sensor 20 and the processing unit 1. However, data transfer between the sensor 20 and the processing unit 1 may also be conducted in a wireless fashion or in other ways.

After (or shortly before) connecting the processing unit 1 to the catheter 2, the processing unit 1 automatically recognizes the catheter 2 using a unique identifier code ID. This code ID may be provided on the catheter 2 or on a package of the catheter 2 and may be input manually into a user interface 4a of a computer device 5 that communicates with the processing unit 1 or may be scanned by means of the device 5 (or by means of a separate scanner connected to the device 5).

Particularly (cf. also FIGS. 2 and 3), the identifier code ID may be matched to information provided in a remote database 60 that can be maintained on a computer network 6 (so-called cloud) or to information that is provided in a memory 10b of the processing unit 1 itself.

Once the catheter 2 is identified in this way, the processing unit 1 is allowed to retrieve information on the recognized catheter 2 and transmits this information to the computer device 5 for displaying it on its display 4. The physician/user of the catheter 2 can confirm the displayed information via a user input into the user interface 4a of the device 5 so as to start a procedure during which the physician will operate the catheter 2 guided by the processing unit 1/system 100. During operation of the catheter 2, the measurement data of the sensor 20 will be send to the processing unit 10 which calibrates the measurement data M based on calibration data C provided in the database 60 and/or in the memory 10b. Particularly, actual (calibrated) measurement data M of the sensor 20 or quantities derived therefrom can be shown on the display 4 in real-time to guide the physician during the procedure using the catheter 2.

Particularly, the information retrieved by the processing unit 1 and shown on the display 4 can contain information about the make and model of the catheter 2, instructions for use (IFU) regarding the catheter 2, the type of the catheter (e.g. balloon catheter for angioplasty etc.), a list of the measurements that can be performed with the catheter 2 or a list of the sensor(s) 20 provided on the catheter 2. For instance, the information can state that the catheter 2 allows to measuring an outer diameter of the balloon 3 using the sensor 20.

Figure 2:
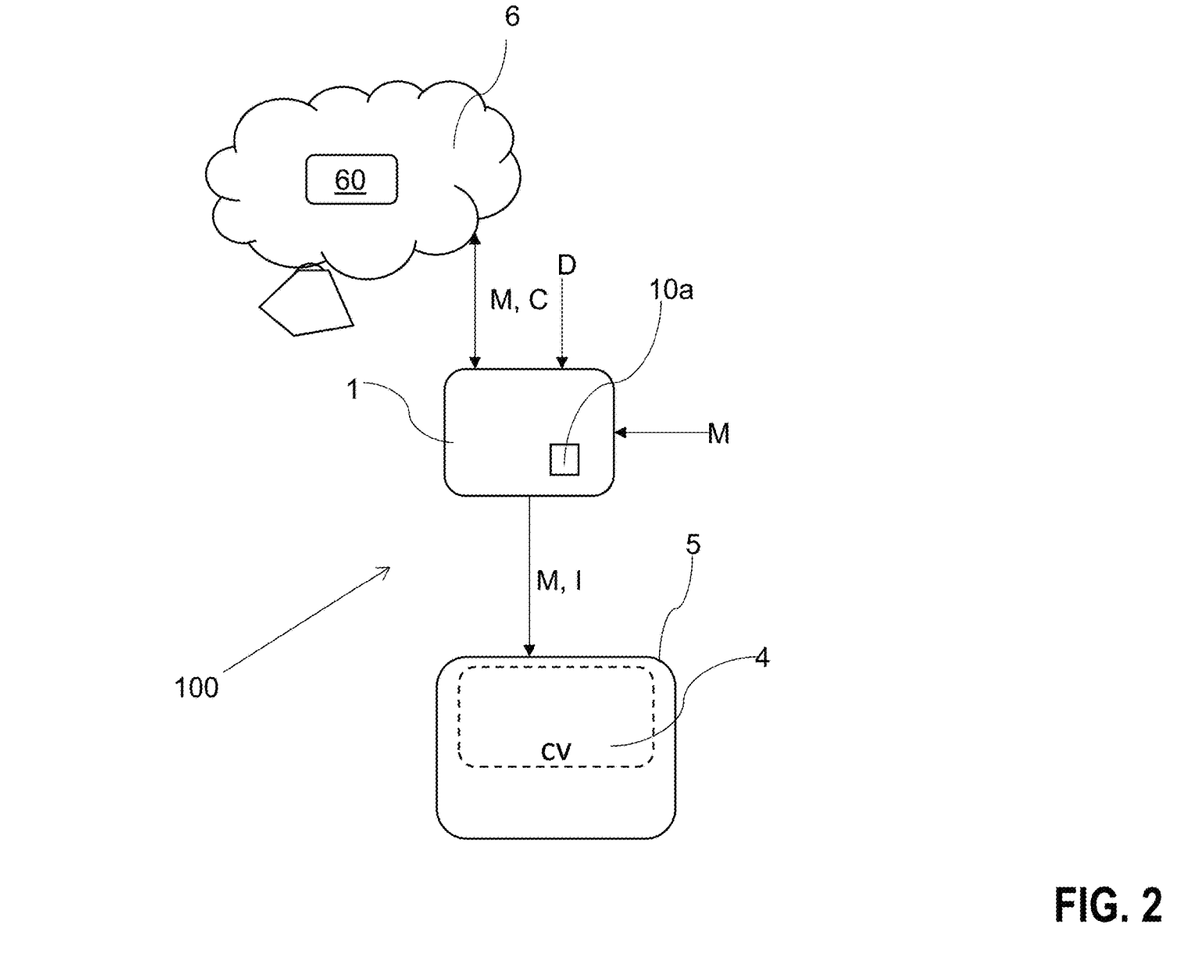
FIG. 2 shows a schematic illustration of a further embodiment of a system according to the present invention.

FIG. 2 shows an embodiment of a system 100 according to the present invention, wherein the system 100 includes a processing unit 1, a database 60 (e.g. provided on a computer network 6), a computer device 5 including a display 4, and particularly a catheter 2 not shown in FIG. 2.

Particularly, the processing unit 1 is configured to receive data D including e.g. codes for identifying a type of the catheter 2 and its type of sensor(s) 20 as well as instructions of use (IFU) relating to the catheters. Furthermore, the processing unit 1 is configured to receive the measurement data or values M coming from the sensor(s) 20 of the catheter 2. Particularly, the catheter 2 can be a balloon catheter including a sensor 20 measuring a parameter that correlates well with the outer diameter of the balloon. However, the processing unit 1 may also be paired with an ablation catheter or any other catheter.

Furthermore, the processing unit 1 is configured to use the provided codes D to calibrate the measurement data M using its integrated circuit 10a/processor 10a. The calibrated measurement data M is transmitted to the computer device 5 and displayed on the display 4 of the device 5 during operation of the catheter 2. The device 5/display 4 is also configured to show information about the catheter 2 such as the maximal pressure of a balloon 2 of the catheter 2 (in case the catheter 2 is a balloon catheter) as well as information contained in the instructions for use (IFU).

Furthermore, according to FIG. 2 data measurement data M could be transmitted to database 60 as well. The database could possibly transmit measurement data M derived from similar catheters to the processing unit. Such data could be used to suggest and display an optimal use of the catheter via the computer device 4 and the display 4. Furthermore calibration data C could be transferred to the processing unit and stored there, which makes more catheters or type of catheters compatible with the processing unit. In the same way calibration data C could be deleted from the processing unit, if the corresponding type of catheter is no longer used . . . .

Figure 3:
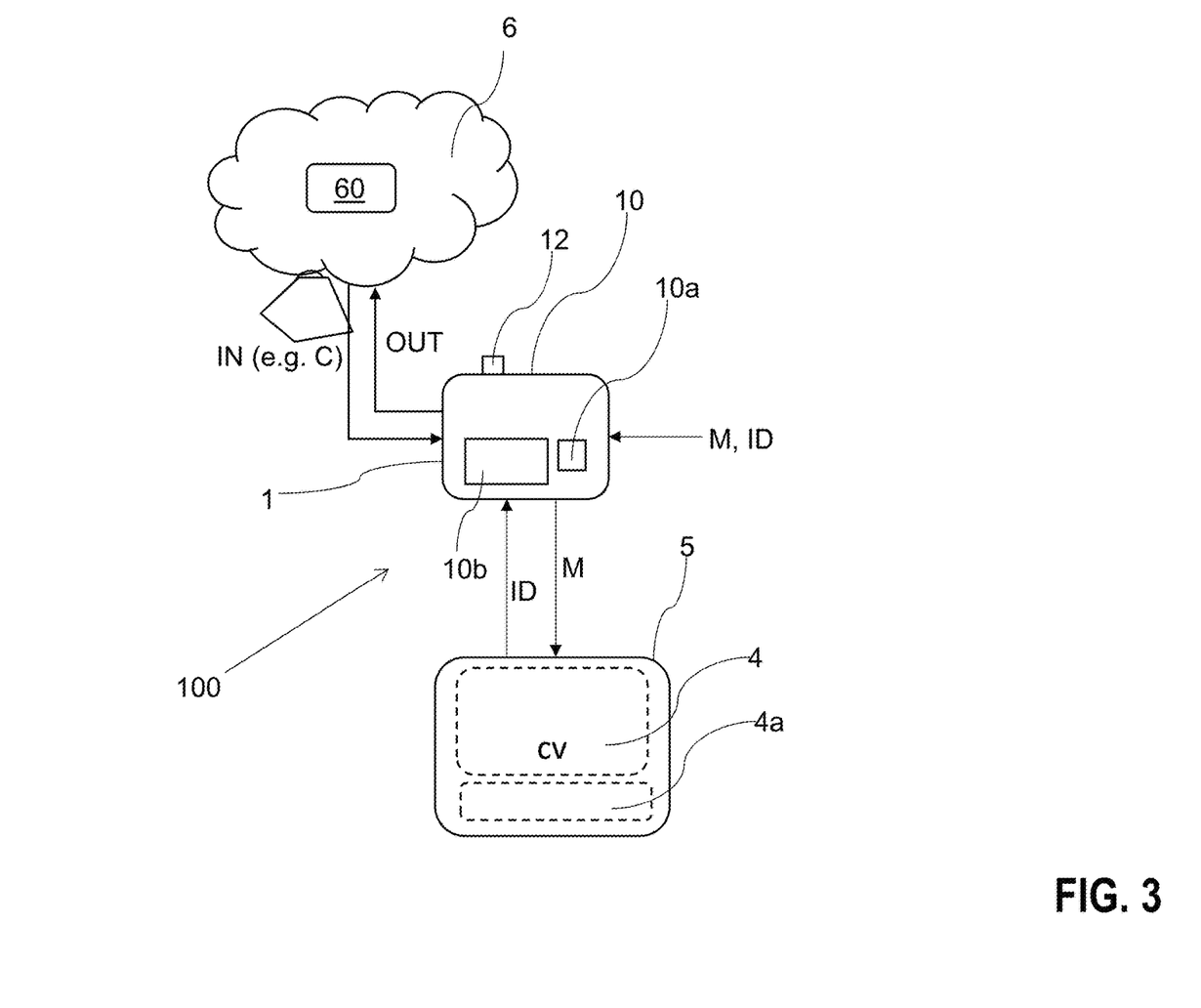
FIG. 3 shows a schematic illustration of a further embodiment of a system according to the present invention.

FIG. 3 shows a further embodiment of a system 100 according to the present invention, wherein the system 100 includes a processing unit 1, a database 60 (e.g. provided on a computer network 6), a computer device 5 including a display 4, and particularly a catheter 2 not shown in FIG. 3.

Particularly, the processing unit 1 is configured to be mechanically connected to the catheter 2, e.g. via suitable one or more suitable connectors 12

According to the embodiment shown in FIG. 3, the bulk of the data is preferably stored/provided in the remote database 60/computer network 6. Particularly, the identifier code ID for identifying/recognizing the respective catheter 2 to which the processing unit 1 shall be connected can be input into the processing unit 1, particularly into the memory 10b, via a user input into a user interface 4a of computer device 5 or by scanning the identifier code ID as described in conjunction with FIG. 1.

During the procedure, the measurement data M from the sensor 20 is calibrated by the processing unit 1 using calibration data C retrieved from the database 20. The calibrated measurement data M is passed to the device 5 for displaying the measurement data M in a preferably continuous fashion during a procedure using catheter 2.

Furthermore, the measurement data M is also stored in the memory 10b of the processing unit and/or passed to the databank 60 for storage and/or later analysis.

Particularly, the processing unit 1 is configured to retrieve information on the recognized catheter 2 denoted as incoming data IN from the databank 60 such as IFU information, particularly work instruction(s) about the recognized/identified catheter 2, the type of the catheter, the purpose of use of the catheter 2 and the type of measurement that the catheter 2 is configured to perform (using e.g. the sensor 20), the type of sensor(s), calibration data C for calibrating the sensor(s)/measurement data M.

Furthermore, the processing unit 1 is configured to upload outgoing data OUT to the databank 60, wherein the outgoing data OUT can include data such as the measurement data M, the type of the catheter 2, other procedural info, for example a duration of the procedure performed with the catheter 2.

Figure 4:
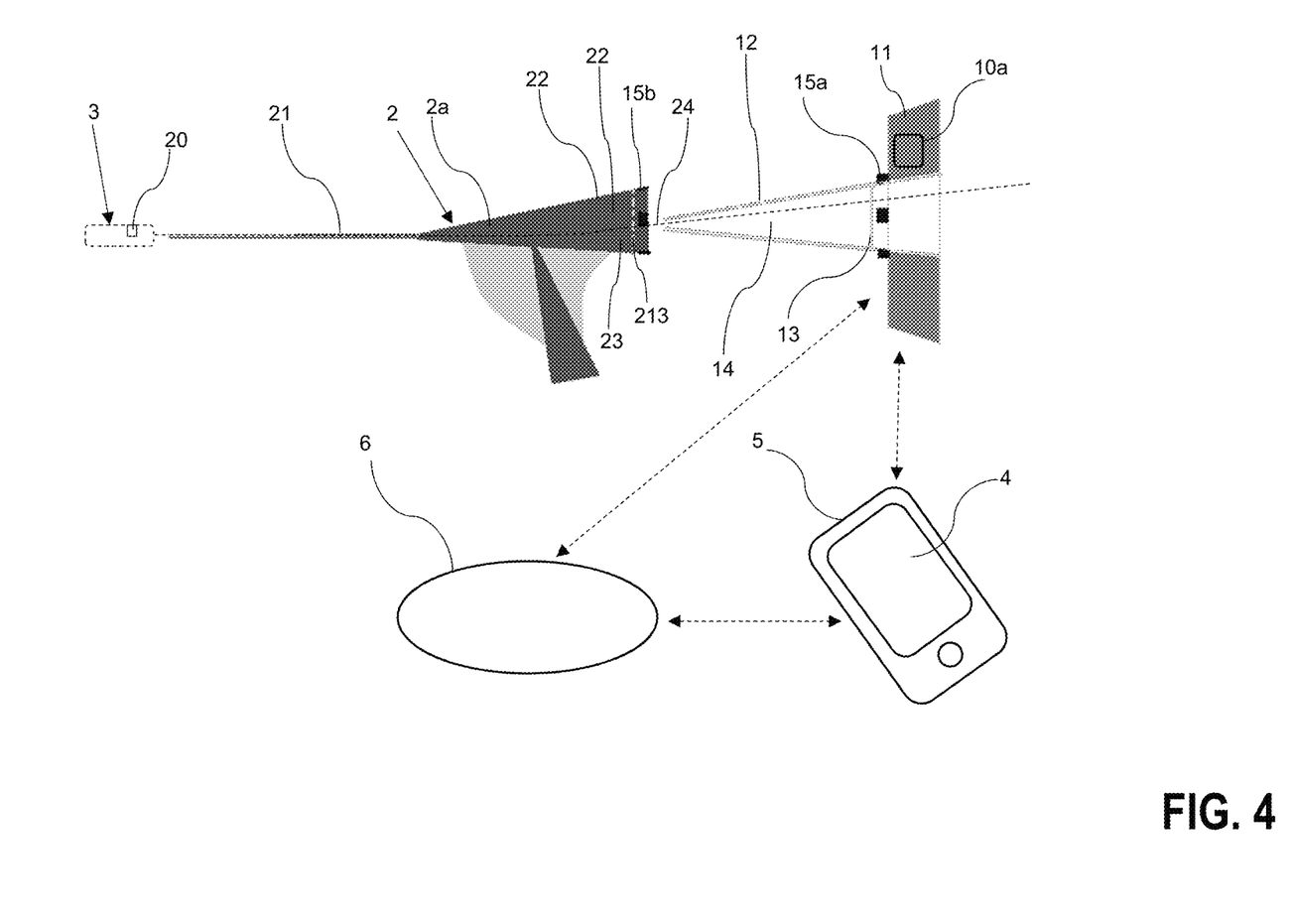
FIG. 4 shows a schematic representation of an embodiment of a processing unit according to the present invention.
Figure 5A:
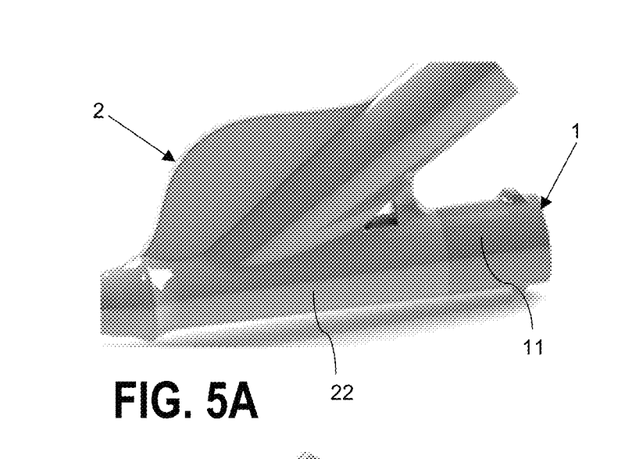
FIGS. 5A-5D show a further embodiment of a processing unit according to the present invention, wherein (5A) shows a perspective view of the processing unit connected to a catheter, (5B) shows a sectional view of the catheter and the processing unit connected thereto, and (5C) and (5D) show the catheter and the processing unit detached therefrom.
Figure 5B:
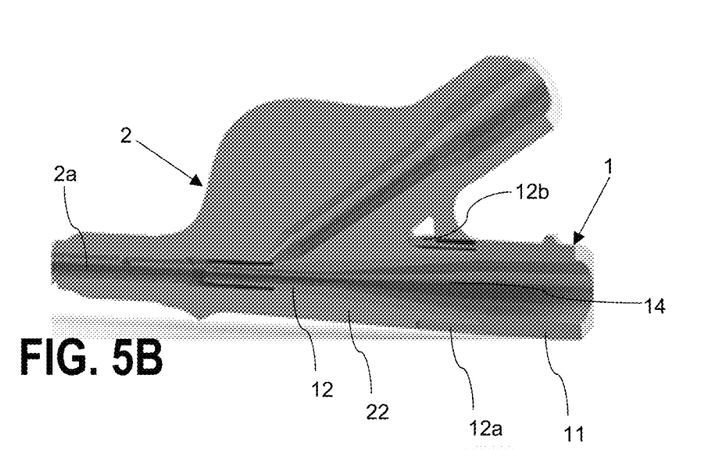
Figure 5C:
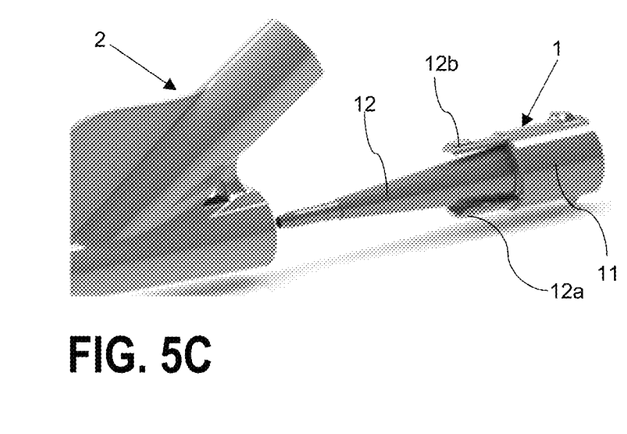
Figure 5D:
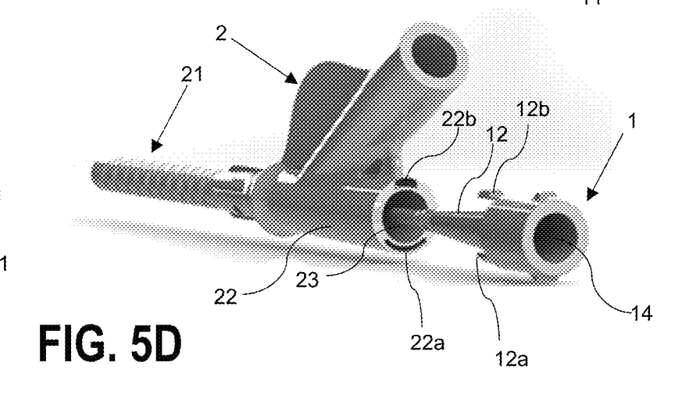

FIG. 4 shows a schematic representation of an embodiment of a processing unit 1 according to the present invention. As before, the processing unit 1 is configured for use with a catheter 2 that may include an inflatable a balloon 3 (e.g. in order to expand a stent in the radial direction in the vessel during angioplasty and to anchor it therewith). Furthermore, the processing unit 1 preferably includes a processor/integrated circuit 10a for processing measurement data M of a sensor 20 arranged on the balloon 3 of the catheter 2, wherein the processing unit 1 is designed to transmit the processed measurement data M via a data link V to a display 4 for displaying the processed measurement data. The sensor 20 can in particular be designed to provide measured values with regard to the radial expansion of the balloon 3.

Furthermore, the processing unit 1 includes a housing 11 which accommodates the processor 10 to protect it, the housing 11 being designed to be releasably connected to the catheter 2 in such a way that a mechanical connection is established between the catheter 2 and the housing 11 and an electrical connection is established between the sensor 20 and the processing unit 1 via which measurement data M can be transmitted from the sensor 20 to the processing unit 1.

To establish the mechanical connection, the housing can have 11 latching lugs 15a, which can engage with latching lugs 15b on the catheter. Alternatively, latching lugs 15b can be fitted on catheter 2; the housing 11 then has corresponding latching recesses 15a. Other positive and/or non-positive fasteners can also be used. The fact that the mechanical connection between the housing 11 and the catheter 2 is releasable means in particular that processing unit 1 can be manually released from catheter 2 (and preferably without using a tool) without damaging the processing unit 1 or the catheter 2.

Due to the releasable mechanical connection and in particular due to the fact that processing unit 1 can adapt the measurement data M of sensor 20 using integrated circuit 10a, the processing unit 1 can be used multiple times, i.e., can be used for different catheters 2, wherein the measurement data is calibrated by the processing unit 1 and displayed to the user/physician via the display 4.

Also here, calibration data used for calibration of the measurement data can be downloaded from a database 60 of a remote computer network 6 or may be provided in a memory of the processing unit 1.

In addition to the measurement data of the sensor 20, the physician is preferably shown all further information about the catheter 2 (e.g. operating instructions, size, etc.) on display 4. The selection of which parameters should be displayed can preferably be determined individually by the physician or hospital staff. All measurement data is preferably not only displayed, but sent to the database of the computer network 6, stored and thus documented.

As can be seen from FIGS. 4 and 5, the processing unit 1 preferably includes a connector portion 12 provided on the housing 11, which can be inserted into an opening 23 of a proximal end section 22 of an outer shaft 21 of catheter 2. The connector portion 12 and the opening 23 can form a two-part Luer system.

Furthermore, it is preferably provided that the connector portion 12 has electrically conductive contacts 13 which are each configured to contact an associated contact 213 of the catheter 2 in order to establish the electrical connection when the connector portion 12 is inserted into the opening 23.

The signals of the sensor 20 are transmitted along the outer shaft 21 via the contacts 213, 13 to the processing unit 1. At the same time, the sensor 20 can be supplied with power via this connection and can record measurement data accordingly. These analog lines are preferably routed to the end of a hypotube of the outer shaft 21.

In particular, the entire electronics of the processing unit 1 can be accommodated in integrated circuit 10a according to an embodiment. This applies in particular to an A/D conversion, an amplifier, a filter, a communication unit for establishing the data connection with the computer device 5 or with the computer network 6, an energy storage as well as an integrated circuit for the calibration/processing of the measurement data of the sensor 20.

As further shown in FIGS. 5A-5D, the housing 11 can have a first projection 12a projecting along the connector portion 12 according to an embodiment of the processing unit 1, which can positively engage in a first recess 22a of the proximal end section 22 to guide the connector portion 12. The housing 11 may also have a second projection 12b adapted to engage and lock into a second recess 22b of the end portion 22 to provide a snap-in connection to the catheter 2.

In both embodiments as shown in FIGS. 4 and 5A-5D, the connector portion 12 and the housing 11, respectively, of the processing unit 1 each surround a through-opening 14, the through-opening 14 being adapted to open into a lumen 2a of the catheter 2 when the connector portion 12 is inserted into the opening 23 of the catheter 2. In this sense, the housing 11 of the processing unit 1 is especially ring-shaped. Balloon 3 and inner shaft 24 are shown in FIG. 1 with dashed lines.

The advantage of the present invention lies in the comparatively simple provision of completely processed sensor signals of a sensor 20 of a catheter 2 that allows to provide guidance to a physician using only a single multi-use processing unit 1 that can be connected to various catheters, is able to recognize the individual catheter 2 and particularly to calibrate measurement data provided by the respective catheter. Particularly, these functions are carried out in conjunction with a remote database and a computer device such as a smartphone. Particularly, since the processing unit 1 can be attached externally to the catheter 2, it can be easily used and reused for different (balloon) catheters 2, which significantly reduces costs and production effort. Despite the calibration of each catheter 2, it is possible to mount only the sensor 20 and the supply and discharge lines on the catheter 2, as the processing unit 1 can be used several times. The processing unit allows the associated calibration to be assigned to each catheter 2 or balloon 3, thus generating the correct sensor signal. In addition, data can be automatically documented and all important parameters for the procedure and handling can be given to the physician. Due to the plug-in connection, the inventive processing unit 1 is particularly easy to handle and does not interfere during the procedure.

The invention claimed is:

1. A processing system including a processing unit for a catheter comprising:
   a housing containing the processing unit;
   a connector portion of the housing configured to be insertable into an opening of a proximal end portion of the catheter, the connector being configured to be connected to the catheter in a releasable fashion and configured to exchange measurement and calibration data (M, C) with a component of the catheter and at least one of a database, a computer network, and a computer device, wherein the processing unit comprises an integrated circuit for processing said data, wherein the connector portion comprises electrically conductive contacts each configured to contact an associated contact of the catheter, wherein the proximal end portion of the catheter comprises a proximal opening of an outer shaft of the catheter and wherein the connector portion and the proximal opening form a two-part Luer system,
   wherein the connector portion comprises first and second projections configured to guide, engage and form a snap-in connection with first and second recesses of the proximal end portion of the opening of the outer shaft of the catheter, and wherein openings of the first and second recesses have different dimensions.

2. The processing system of claim 1, wherein said component is one or more of: a sensor and an inflation pump for inflating a balloon.

3. The processing system of claim 1, wherein the processing unit is configured to recognize the catheter using an identifier code (ID) of the catheter.

4. The processing system of claim 1, wherein the processing unit comprises a memory for storing information relating to different catheters.

5. The processing system of claim 4, wherein the processing unit is configured to compare the identifier code (ID) with information stored in said memory or with information stored in a remote database.

6. The processing system of claim 5, wherein the processing unit is configured to retrieve information concerning a recognized catheter from the memory and/or from the remote database and to transmit said retrieved information to a computer device to display said information on a display of the computer device.

7. The processing system of claim 6, wherein the processing unit is configured to retrieve calibration data (C) corresponding to the recognized catheter from the memory or from the remote database and to calibrate the measurement data (M) of the sensor using the calibration data (C).

8. A catheter system comprising a processing system according to claim 1 and a catheter comprising a sensor for measuring a parameter relating to the catheter.

9. The catheter system of claim 8, comprising a computer device configured to communicate with the processing unit.

10. The catheter system of claim 9, the computer device comprises a user interface and a display configured for graphically displaying information.

11. The catheter system of claim 10, wherein the computer device is configured to scan the identifier code (ID) from the catheter or a package of the catheter, and/or wherein the user interface is configured to receive the identifier code (ID) as a user input.

12. The catheter system of claim 10, comprising a database implemented on a computer network.

13. The catheter system of claim 10, the processing unit is configured to transmit retrieved information concerning the catheter to the computer device, which is configured to display said retrieved information via said display.

14. The catheter system of claim 10, wherein the user interface is configured to receive an input by the user to confirm use of the recognized catheter.

15. The catheter system of claim 10, wherein the processing unit is configured to transmit measurement data (M) received from the sensor to the computer device to display the measurement data (M) on said display during operation of the catheter.

16. The catheter system of claim 8, wherein the processing unit is configured to store the measurement data (M) received from the sensor and/or data relating to a procedure performed with the catheter in the memory of the processing unit and/or in the database.

17. A method of using the catheter system of claim 8, the method comprises the steps of:
   connecting the processing system to a catheter in a releasable fashion with the connector portion,
   automatically recognizing the catheter using an identifier code (ID) of the catheter,
   retrieving information with the processing unit about the recognized catheter from the memory of the processing unit or from the database, and displaying measurement data (M) transmitted by the sensor of the catheter to the processing unit on the display of the computer device.

\* \* \* \* \*